United States Patent [19]

Frank et al.

[11] Patent Number: 5,203,775
[45] Date of Patent: Apr. 20, 1993

[54] NEEDLELESS CONNECTOR SAMPLE SITE

[75] Inventors: Thomas P. Frank, Dublin; Charles R. Patzer, Columbus, both of Ohio

[73] Assignee: Medex, Inc., Dublin, Ohio

[21] Appl. No.: 855,147

[22] Filed: Mar. 20, 1992

Related U.S. Application Data

[63] Continuation of Ser. No. 584,286, Sep. 18, 1990, abandoned.

[51] Int. Cl.$^5$ ............................................. A61M 5/00
[52] U.S. Cl. ................................... 604/256; 604/283; 604/905; 251/149.1
[58] Field of Search ............................. 604/83, 86–88, 604/167, 200–202, 205–206, 236–237, 244, 249, 256, 283, 905; 251/149.1

[56] References Cited

U.S. PATENT DOCUMENTS

| | | |
|---|---|---|
| 2,653,606 | 9/1953 | Ryan . |
| 3,057,350 | 10/1962 | Cowley . |
| 3,157,201 | 11/1964 | Littman . |
| 3,620,500 | 11/1971 | Santomieri . |
| 3,837,381 | 9/1974 | Arroyo .................................. 141/350 |
| 3,856,010 | 12/1974 | Moorehead et al. . |
| 3,856,020 | 12/1974 | Kovac . |
| 3,875,938 | 4/1975 | Mellor . |
| 3,898,988 | 8/1975 | Morgan . |
| 4,006,744 | 2/1977 | Steer . |
| 4,105,500 | 8/1978 | Libman et al. . |
| 4,106,491 | 8/1978 | Guerra . |
| 4,143,853 | 3/1979 | Abramson . |
| 4,149,535 | 4/1979 | Volder . |
| 4,177,809 | 12/1979 | Moorehead . |
| 4,200,096 | 4/1980 | Charvin . |
| 4,219,021 | 8/1980 | Fink . |
| 4,252,122 | 2/1981 | Halvorsen . |
| 4,341,224 | 7/1982 | Stevens . |
| 4,387,879 | 6/1983 | Tauschinski . |
| 4,457,753 | 7/1984 | Pastrone . |
| 4,512,766 | 4/1985 | Vailancourt . |
| 4,610,665 | 9/1986 | Matsumoto et al. . |
| 4,683,916 | 8/1987 | Raines . |
| 4,781,702 | 11/1988 | Herrli . |
| 4,838,855 | 6/1989 | Lynn . |
| 4,842,591 | 6/1989 | Luther . |
| 4,865,583 | 9/1989 | Tu . |
| 4,871,356 | 10/1989 | Haindl et al. . |
| 4,874,377 | 10/1989 | Newgard et al. . |
| 4,895,346 | 1/1990 | Steigerwald . |
| 4,935,010 | 6/1990 | Cox et al. . |
| 4,960,412 | 10/1990 | Fink . |
| 5,006,114 | 4/1991 | Rogers et al. . |

FOREIGN PATENT DOCUMENTS

| | | |
|---|---|---|
| 0223451 | 5/1987 | European Pat. Off. . |
| 0309771 | 4/1989 | European Pat. Off. . |
| 0343953 | 11/1989 | European Pat. Off. . |
| 3031242 | 3/1982 | Fed. Rep. of Germany . |
| 3303718 | 10/1984 | Fed. Rep. of Germany . |
| 2049513 | 3/1971 | France . |
| 8906553 | 8/1989 | PCT Int'l Appl. . |
| WO9011103 | 10/1990 | PCT Int'l Appl. . |

OTHER PUBLICATIONS

International Search Report in PCT/US91/06604.

Primary Examiner—John D. Yasko
Assistant Examiner—C. Maglione
Attorney, Agent, or Firm—Wood, Herron & Evans

[57] ABSTRACT

A sample site having a needleless connector access port including a flush mounted valve assembly which is readily accessible for wiping clean with a disinfectant. A male Luer connector may be operatively connected into the access port by a split Luer arrangement of female Luer connector portions adjacent the access port aperture. The split Luer arrangement does not generally obstruct wiping access to the access port and may include moveable connector portions to provide completely unobstructed wiping access thereto.

34 Claims, 3 Drawing Sheets

NEEDLELESS CONNECTOR SAMPLE SITE

This application is a continuation of application Ser. No. 07/584,286, filed Sep. 18, 1990 now abandoned.

FIELD OF THE INVENTION

This invention relates to sample sites through which fluids are injected or withdrawn from a patient's circulatory system and, more particularly, to such a sample site which does not require use of a needle for injecting or withdrawing samples and in which the access port is easily reached for disinfecting.

BACKGROUND OF THE INVENTION

Sample sites for obtaining fluid access to a patient's circulatory system are well known. For example, a catheter inserted into a patient's blood vessel may be connected to a sample site such as shown in U.S. Pat. No. 4,874,377, the disclosure of which is fully incorporated herein by reference. Alternatively, the sample site may be in-line with tubing connecting the catheter to a blood pressure monitoring transducer and/or a supply of saline or other solution, such as shown in co-pending application Ser. No. 577,153 filed Sep. 4, 1990 mailed Aug. 30, 1990 and received in the U.S. Patent and Trademark Office Sep. 4, 1990, entitled "Method and Apparatus for Sampling Blood," in the name of Phillip D. Messinger (the "Messinger application"), and which is a continuation-in-part of Ser. No. 07/524,224 filed May 15, 1990, now U.S. Pat. No. 5,048,537, the disclosures of which are fully incorporated herein by reference.

Typical of sample sites is that they include a housing having a liquid path extending therein and which is to be coupled to the patient's circulatory system to make the fluid connection such as through a catheter and/or the tubing of an intravenous system, for example, like the blood pressure monitoring apparatus shown in the aforementioned patent applications. A sample site further typically includes an access port through which fluids may be introduced into the patient's circulatory system or from which blood may be withdrawn from the patient, both via the liquid path. By way of example, a needle may be received through a resilient stopper in the access port and on into the liquid path to couple a syringe or the like attached to the needle with the patient's circulatory system for injection/withdrawal of fluids. However, sampling sites requiring use of a needle present significant risks from needle sticks. As will be readily appreciated, needle sticks provide a mechanism for transfer of dangerous diseases, such as hepatitis or AIDS.

To reduce risk of needle sticks, sampling sites have been developed which eliminate needles. Such sampling sites provide an access port adapted for needleless connection with an external fluidic system such as a syringe or tubing. To this end, a cylindrical reservoir is provided on the sample site to provide a confined conduit between the needleless connector such as a male Luer connector and a valve assembly within the sample site. One example is the stopcock side port shown in FIG. 5 in the aforementioned Messinger application in which the external fluidic system is connected thereto by securing the cuff of a male Luer lock connector to the flanged top of a reservoir defined by the cylindrical wall of a female Luer connector. Other needleless access ports are provided in which a blunt cannula, such as the tip or taper of a male Luer connector, is receivable into the cylindrical reservoir. As shown, for example, in aforementioned U.S. Pat. No. 4,874,377, the male Luer connector tip impacts the valve assembly at the bottom of the female Luer connector reservoir causing the valve to deflect and open under pressure of the tip of the male Luer connector thereagainst. As the valve assembly opens, a channel for fluid communication between the liquid path within the sample site and the external fluidic system is created.

While such needleless sample sites reduce or eliminate needle stick problems, the cylindrical reservoir by which to secure the male Luer connector to the sample site has introduced its own significant problems. In particular, the reservoir is difficult to clean and has prompted concern about contamination and the dangers of bacterial growth therein.

SUMMARY OF THE INVENTION

The present invention provides the benefits of a needleless sample site, while reducing the risk of contamination and bacterial growth. To this end, and in accordance with the principles of the present invention, the reservoir above the valve assembly is eliminated and replaced with arms extending above the access port to provide the function of guiding a blunt cannula such as a male Luer connector tip against the seal, but without a reservoir wall to obstruct ready access to the surface of the valve assembly for disinfecting. The arms may be flanged to provide the function of locking a male Luer lock connector thereto.

More specifically, the access port is defined by an apertured exterior wall of the sample site housing through which a blunt cannula such as the tip of a male Luer connector is to be received. The outer surface of a seal member contained within the housing normally blocks the aperture. The exterior wall adjacent the aperture and the outer surface of the seal member are easily wiped clean and, thus, may be considered to be generally flush in the closed position of the seal member. Consequently, there is no reservoir defined about the aperture and seal surface from which contaminants or bacteria may be difficult to remove. The seal member is deflectable under pressure of the tip of a male Luer connector passing into the aperture so as to open the seal member and provide fluid access to the liquid path in the sample site. When the male Luer connector is withdrawn, the seal shuts to again block the aperture, but because there is no confined reservoir above the aperture, the exposed surface of the seal member and portions of the exterior wall adjacent the aperture (as well as the flanged arms) are readily accessible to a clinician for purposes of disinfecting the access port, such as by a wiping action between the flanged arms in a direction generally parallel the seal member and/or exterior wall surfaces. Consequently, there is less opportunity for contamination or bacterial growth with the sampling site of the present invention.

The female Luer connector function is provided atop the access port but without the cylindrical reservoir normally provided thereby. To this end, a pair of arms are provided adjacent the access port aperture so as to matingly receive the male Luer connector tip therethrough while still providing generally unobstructed wiping access to the outer surface of the seal member and portions of the housing exterior wall adjacent the aperture. The arms may be flanged to lock the male Luer connector thereto such that the arms may be seen as separate portions of a female Luer connector and may thus be referred to as a split Luer arrangement.

According to one aspect of the invention, the female Luer connector portions or flanged arms are fixedly mounted to the housing exterior wall adjacent the aperture such that the inner or confronting surfaces of the flanged arms define an imaginary female Luer connector cylinder about the aperture, but without the impediment of a complete cylindrical wall. According to a further aspect of the invention, the flanged arms are moveable from an operative position about the aperture to provide the female Luer connector function to an inoperative position away from the sample site housing to provide completely unobstructed access to the outer surface of the seal member, as well as to the annular portion of the housing exterior wall completely surrounding the aperture. In accordance with this further aspect of the invention, the flanged arms are mounted to the end of hinge arms so as to be moveable toward and away from the aperture. The hinge arms may be fixedly connected at their extreme ends to the housing and remote from the aperture and normally biased to urge the flanged arms away from the aperture. The hinge arms may then be compressed toward the sample site housing bringing the flanged arms adjacent the aperture for connecting to the male Luer connector. Alternatively, the hinge arms may be slidably connected to the housing for sliding the flanged arms between the operative and inoperative positions. With the hinge arms connected to a frame member slidably disposed on a side of the housing opposite the access port, the hinge arms will ride along the side of the housing therebetween. In that event, the hinge arms are normally biased toward the housing to urge the flanged arms toward the aperture. As the frame member slides away from the access port, the hinge arms are pushed apart by the housing to separate the flanged arms and allow them to pass down over the side of the housing completely exposing the exterior wall and seal surface for disinfecting.

By virtue of the foregoing, there is thus provided a sample site with a flush-mounted needleless access port and a split Luer arrangement so as to properly connect a male Luer connector to the access port, but without obstructing wiping access to the seal member and surrounding regions of the housing for purposes of disinfection.

These and other objects and advantages of the present invention shall be made apparent from the accompanying drawings and description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION OF THE DRAWINGS

Figure 1:
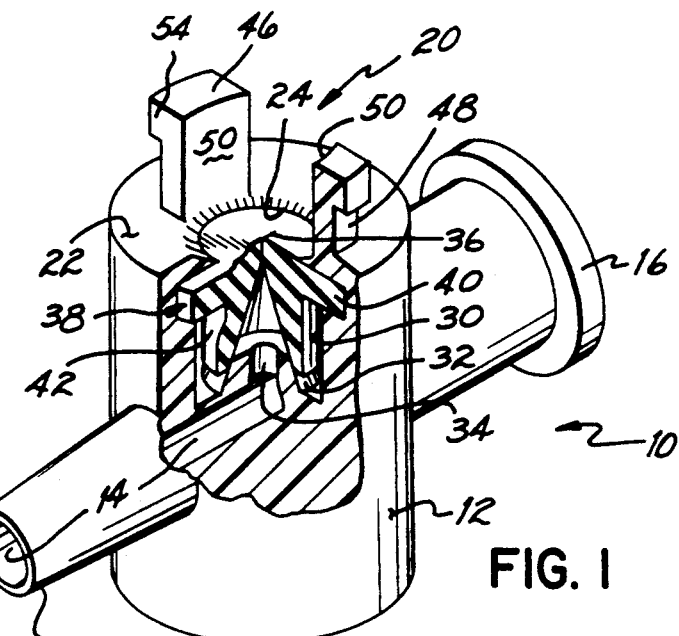
FIG. 1 is a perspective view of a first embodiment of a sample site in accordance with the principles of the present invention.
Figure 2:
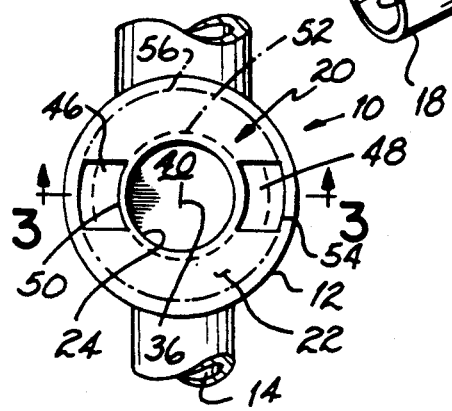
FIG. 2 is a top plan view of the sample site of FIG. 1.
Figure 3:
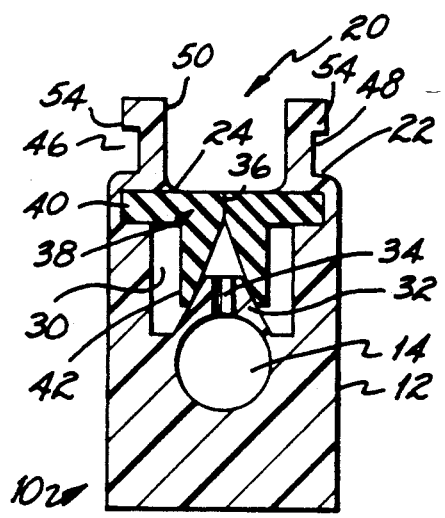
FIG. 3 is a cross-sectional view of the sample site of FIG. 1 along line 3—3 of FIG. 2.

With reference to FIGS. 1-4, there is shown one embodiment 10 of a sample site in accordance with the principles of the present invention. Sample site 10 is defined by a cylindrical housing 12 having a liquid path 14 extending therein. At opposite ends of path 14 are female Luer connector port 16 and male taper port 18 for connection with tubing or the like, such as for fluid communication with a patient's circulatory system (see FIG. 7). Housing 12 includes a needleless connector access port 20 between ports 16 and 18 defined along generally planar, top exterior wall 22 of housing 12. Wall 22 includes an aperture 24 through which is to be received a blunt cannula such as the tip or taper 26 of a male Luer connector 28 for fluid communication with liquid path 14. Aperture 24 is sized to closely surround tip 26 when received therethrough.

A valve assembly is provided at aperture 24 and within recess 30 of housing 12 between top wall 22 and liquid path 14 by frustro-conical actuating member 32 fixedly positioned within housing 12 and a seal member 38. Actuating member 32 includes a lumen 34 therethrough transverse to and in fluid communication with liquid path 14. Lumen 34 is aimed at and sealed-off by normally closed channel 36 of resilient seal member 38 positioned over actuator member 32. Seal member 38 includes hub 42 extending below seal upper surface 40 and seated over actuating member 32. The top surface 40 of seal member 38 is generally flush top wall 22 when it is closed against or adjacent aperture 24. In this regard, the thickness of wall 22 adjacent aperture 24 is relatively thin in comparison to the length of the male Luer connector tip 26 so as not to define a reservoir wall relative tip 26. Exterior wall 22 may be about 0.035-0.040 inches thick such that a wipe (not shown) passed across wall 22 will easily disinfect wall 22 and surface 40 without creating a well or reservoir for contaminants or bacteria to accumulate out of reach of the wipe as it passes across top wall 22. Alternatively, surface 40 may protrude from aperture 24. Thus, it will be appreciated that upper surface 40 of seal member 38 may be considered generally flush top wall 22 in the closed position inasmuch as the surface of the valve assembly is readily accessible to be wiped with disinfectant by wiping across top wall 22 from one side to the other.

As generally described in aforesaid U.S. Pat. No. 4,874,377, under pressure from male lumen connector tip 26 against upper surface 40, seal member 38 deflects toward liquid path 14 and drives hub 42 against the conical surface of projection 32. As hub 42 rides over projection 32, channel 36 is caused to open revealing lumen 34 for fluid communication via tip 26 between liquid path 14 and an external fluidic system coupled to connector 28 such as a syringe 44 or tubing (not shown). When male Luer connector 28 is removed, the resiliency of seal member 36 causes hub 42 to ride up frustro-conical actuating member 32 and reseal aperture 36 with outer surface 40 again adjacent aperture 24 and generally flush top wall 22.

Figure 4:
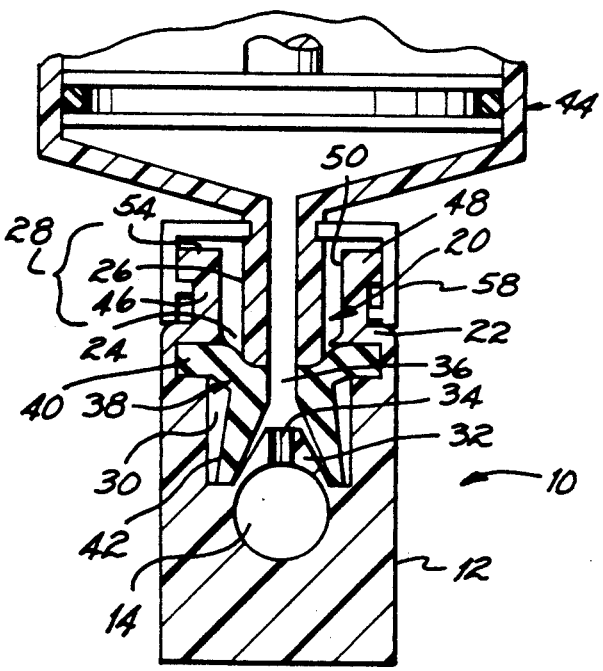
FIG. 4 is a cross-sectional view like that of FIG. 2, but with a syringe coupled thereto via a male Luer connector.

To secure male Luer connector 28 to sample site 10 while not otherwise obstructing wiping access to disinfect the exposed outer surface 40 of seal member 38 in aperture 24 and adjacent portions of external wall 22, a split Luer arrangement is provided. To this end, extending upwardly and away from top wall 22 are a pair of flanged arms 46, 48. Arms 46, 48 are attached to top wall 22 at spaced apart locations adjacent aperture 24 such that the arcuate inner surfaces 50 of the arms define an imaginary cylinder 52 (shown in phantom line in FIG. 2) corresponding to the inner surface of a female Luer connector cylinder. Similarly, flanges 54 of arms 46, 48 define an imaginary flange thread plane 56 (also shown in phantom line in FIG. 2) corresponding to the threading flange of a female Luer connector onto which may be threadably received rotatable threaded cuff 58 of a male Luer lock connector 28, as shown in FIG. 4. Arms 46, 48 thus define a pair of spaced apart female Luer connector portions.

In the embodiment of the invention shown in FIGS. 1–4, inner surface 50 and flange 54 of each arm 46, 48 define approximately fifteen percent (15%) of the circumference of a female Luer connector cylinder and/or flange (a combined total of 30%) to thereby functionally provide the female Luer connector functions of guiding tip 26 and locking connector 28 in place, respectively, while leaving access port 20 otherwise generally unobstructed. Thus, a clinician (not shown) may readily disinfect access port 20 and flange arms 46, 48 by wiping across the surface of top wall 22 such as in the direction from port 16 to port 18 with a disinfectant material such as with an alcohol wipe to disinfect the area about aperture 24. As a consequence, the needleless sample site of the present invention eliminates the need to use needles with their attendant risks, while greatly reducing the risk of contamination and bacterial growth normally of great concern with prior needleless sample sites.

Figure 5:
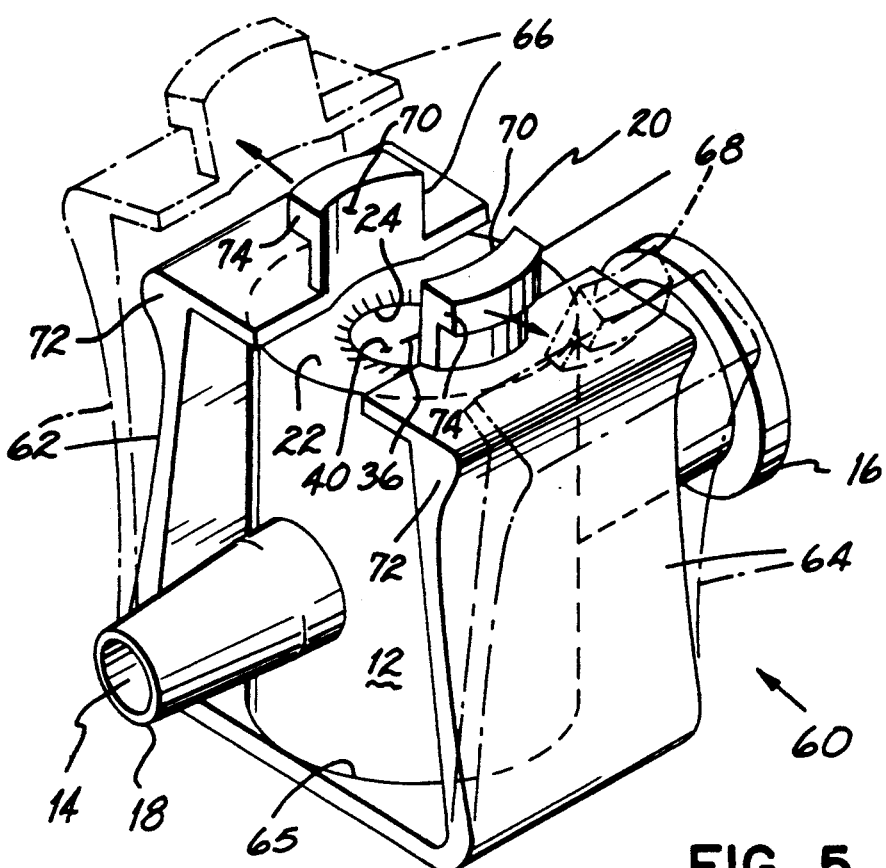
FIG. 5 is a perspective view of a second embodiment of a sample site in accordance with the principles of the present invention.

An alternative embodiment 60 of a sample site in accordance with the principles of the present invention is shown in FIG. 5. Sample site 60 is substantially similar to sample site 10 with the exception of the provision of a modified split Luer connector. In the sample site of embodiment 60, the entire surface of top wall 22 may be completely freed from obstruction by placing the split Luer arrangement in an inoperative position. To this end, the split Luer arrangement of embodiment 60 is provided by a pair of hinge arms 62, 64 connected such as by sonic welding or glue to bottom wall 65 of housing 12 and defining at their extremities a pair of female Luer connector portions or flanged arms 66, 68. Hinge arms 62, 64 may be living hinges and are normally in an inoperative position shown in dashed line in FIG. 5 with arms 66, 68 outwardly of housing 12 so as to expose the entirety of top wall 22 and seal member outer surface 40 (as well as the inner walls 70 of arms 66, 68) to be easily and readily wiped clean for purposes of disinfection.

Hinge arms 62, 64 are thickened as at 72 adjacent flanged arms 66, 68 to provide a convenient place for a clinician (not shown) to grip hinge arms 62, 64 and compress them together to bring female Luer connector portions 66, 68 into an operative position shown in solid line in FIG. 5 to provide the female Luer connector function for receiving a male Luer connector 28 as in the case of connector portions 46, 48 described in connection with sample site 10. When male Luer connector 28 is removed, hinge arms 62, 64 urge the split Luer arrangement apart into the inoperative position. The inner wall 70 and flange 74 of each flanged arm 66, 68 comprise about twenty-five percent (25%) of the circumference of a female Luer connector cylinder and flange, or about fifty percent (50%) total.

Figure 6:
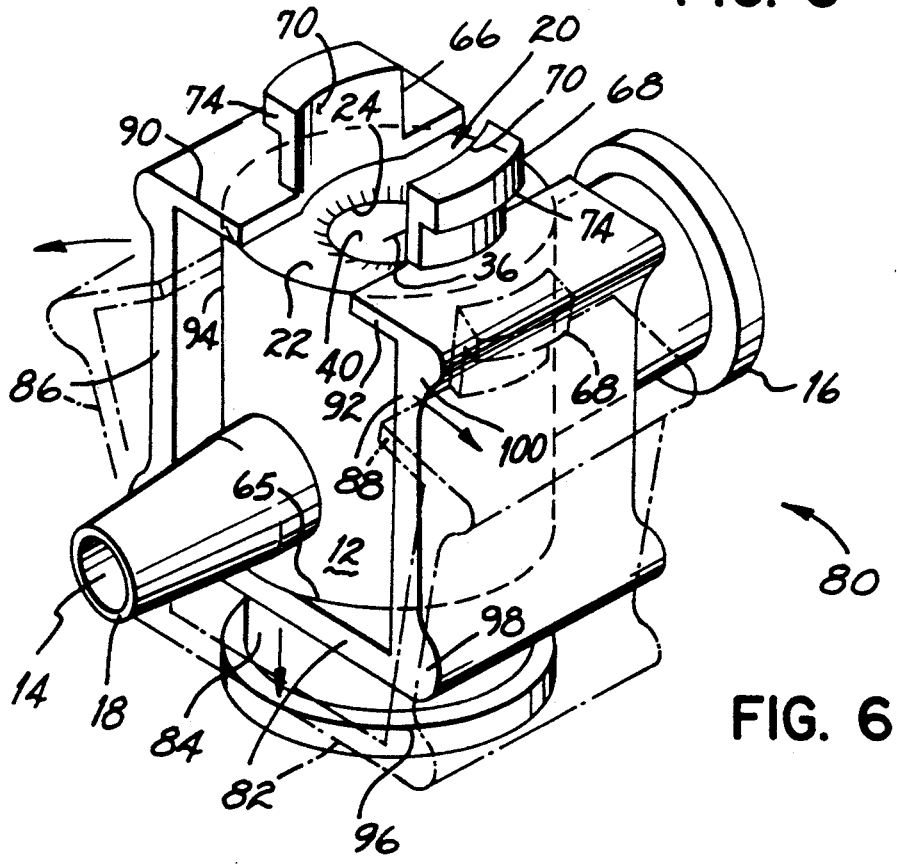
FIG. 6 is a perspective view of a third embodiment of a sample site in accordance with the principles of the present invention.

A yet further alternative embodiment 80 of a sample site in accordance with the present invention is shown in FIG. 6. Sample site 80 is substantially similar to sample site 70 with the exception of the mechanism for moving female Luer connector portions 66, 68 between the operative and inoperative positions shown in solid and dashed line, respectively. To this end, a frame member 82 is slidably supported on an annular extension 84 attached to bottom 65 of housing 12. Attached to frame member 82 are a pair of hinge arms 86, 88 with shelves 90, 92 carrying flanged arms 66, 68, respectively. Hinge arms 86, 88 are normally biased toward side wall 94 of housing 12, such that with frame member 82 slid against bottom 65, shelves 90, 92 pass over housing top wall 22 to position flanged arms 66, 68 into the operative position adjacent aperture 24 to provide the female Luer connector function. To disinfect the access port, frame member 82 is slid away from bottom 65 toward flange wall 96 of annular extension 84. As the frame member is thus moved, top wall 22 and shelves 90, 92 cooperate to urge hinge arms 86, 88 outwardly of housing 12 and away from aperture 24 allowing flanged arms 66, 68 to ride astride housing side wall 94 into the inoperative position completely exposing access port 20 for disinfecting such as by wiping a disinfectant material thereacross. Hinge arms 86, 88 are thickened top and bottom as at 98, 100 to facilitate sliding frame member 82 by finger pressure there-against in the direction desired to slide frame member 82. As shown in FIG. 6, hinge arms 86, 88 thus move in a direction parallel lumen 34 and transverse liquid path 14. The hinge arms could alternatively be mounted to slide parallel liquid path 14 and transverse lumen 34.

By virtue of the foregoing, there is provided a split Luer arrangement to simulate a female Luer connector, but without the reservoir which would otherwise impede ready access to access port 20 including surface 40 of seal member 38 and the adjacent annular portion of top wall 22 completely surrounding exposed surface 40 for disinfecting thereof, to reduce the likelihood that contamination or bacterial growth might occur. Although housing 12 has been shown as a T-connection, the access port and split Luer combination of the present invention may be provided in other types of sample sites. Thus, the liquid path within housing 12 may be coaxial with lumen 34 rather than transverse thereto and may have only one of ports 16, 18 connected thereto. Similarly, ports 16 and 18 could form part of a Y-connector rather than a T-connector. Still further, the flush mounted needleless access port and split Luer lock arrangement could also be provided at each of ports 16, 18.

Figure 7:
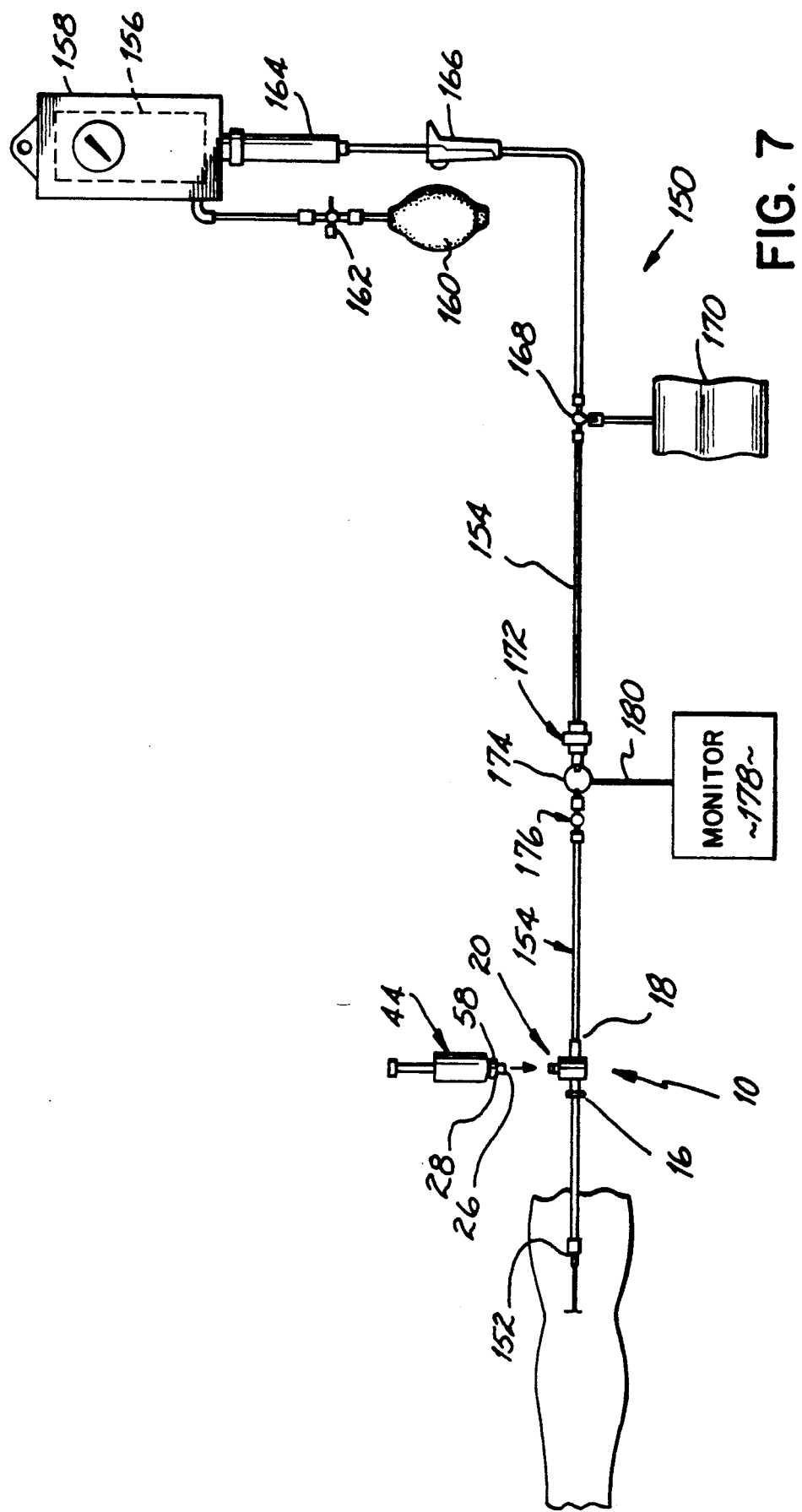
FIG. 7 is a diagrammatic view of an exemplary, closed blood sampling system incorporating a sample site of the present invention.

Use of a sample site of the present invention will be described in connection with a closed blood sampling system 150 as shown in FIG. 7. System 150 includes a catheter 152 for insertion into a patient's blood vessel and connected in a series via tubing 154 to a bag 156 of saline solution. Bag 156 is wrapped in a pressure cuff 158 which may be inflated by an inflation squeeze bulb 160 through a stopcock 162. The solution flows out of bag 156 through conventional drip chamber 164. A roller clamp 166 may be mounted on tubing 154 adjacent drip chamber 164 in order to selectively block the flow of solution from bag 156 toward the patient. Connected immediately downstream of roller clamp 166 is a shunted stopcock 168 coupled to a waste collection bag 170. Downstream of stopcock 168 is a flush device 172, pressure transducer 174, and three-way stopcock 176. Pressure transducer 174 is electrically connected to a monitor 178 by cable 180 for monitoring the patient's blood pressure. A transducer of the type disclosed in U.S. Pat. No. 4,920,972, the disclosure of which is fully incorporated herein by reference, may be employed. Operation of the above is described in greater detail in the aforementioned Messinger applications.

In use, a sample site of the present invention is situated between catheter 152 and three-way stopcock 176 by coupling port 16 to catheter 152 and port 18 to stopcock 176 to continue the in-line fluid path between bag 156 and catheter 152. Syringe 44 may be connected in fluid communication therewith by first wiping access port 20 with a disinfectant and then, if they are movable, placing the female Luer connector portions of the sample site into the operative position. The male Luer connector 28 is then fitted to access port 20 by inserting tip 26 thereof between the inner walls of the split Luer arrangement and into the aperture to deflect seal member 38 and open the valve assembly under pressure of tip 26 to reveal lumen 34 and provide a fluid path between syringe 44 and liquid path 14 coupled to catheter 152. Where the male Luer connector is of the locking type, the cuff 58 thereof may be rotated onto the flanges of the split Luer arrangement to maintain the connection.

After injecting or sampling as desired, syringe 44 is removed by withdrawing male Luer connector tip 26, allowing seal member 38 to reclose. The access port 20 will also be accessible (or made accessible by movement of the female Luer connector portions to the inoperative position) to allow access port 20 to again be disinfected by wiping thereacross.

By virtue of the foregoing, there is thus provided a needleless connector sample site in which the access port is generally unobstructed to provide wiping access for disinfecting, while eliminating the risk of needle sticks common to needle-based sample sites and to improve sterility and reduce risk of infection otherwise feared from prior needleless connector sample sites.

While the present invention has been illustrated by the description of embodiments thereof, and while the embodiments have been described in considerable detail, it is not the intention of applicants to restrict or in any way limit the scope of the appended claims to such detail. Additional advantages and modifications will readily appear to those skilled in the art. It will be understood that the sample site of the present invention may be utilized as an injection site when coupled to the venous side of a patient's circulatory system, as a sample port when connected to the arterial side, or as a link to connect an exterior fluidic system to an otherwise closed fluidic system without opening the closed system, thereby avoiding the possibility of reflux in the closed system. Reference to sample site will thus be appreciated as a reference to any of the above. The blunt cannula could be shrouded or unshrouded. In the former, the shroud (not shown) may be receivable over side wall 94 of housing 12. In the latter, tip 26 may be a typical male Luer slip cannula at the end of syringe 44, but without threaded cuff 58. In either event, the split Luer arrangement may either be merely a pair of unflanged arms or could be eliminated altogether. The invention in its broader aspects is therefore not limited to the specific details, representative apparatus and method, and illustrative examples shown and described. Accordingly, departures may be made from such details without departing from the spirit or scope of applicants' general inventive concept.

What is claimed is:

1. A sample site adapted to connect to a blunt cannula comprising:
   a housing;
   a liquid path extending into the housing;
   an actuator member fixedly positioned within the housing and having a lumen therethrough in fluid communication with the liquid path;
   an apertured exterior wall on the housing through which the blunt cannula can enter the housing to make fluid connection to the lumen;
   seal means adjacent the exterior wall aperture and presenting an outer surface generally flush with an in adjacent contact with the housing exterior wall for normally sealing the aperture against fluid communication with the lumen, the seal means being movable into the actuator member under pressure of the blunt cannula passing into the aperture so as to open a channel in the seal means and expose the lumen therethrough to the blunt cannula, the seal means channel being resealed and the exterior wall and seal means outer surface being substantially unobstructed with the blunt cannula removed.

2. The sample site of claim 1, the housing including at least one port coupled to the liquid path.

3. The sample site of claim 1, the housing including first and second spaced apart ports at respective ends of the liquid path.

4. The sample site of claim 1 further comprising:
   a pair of arms expending away from the housing about the aperture for receiving the blunt cannula therethrough, the arms being spaced apart to facilitate cleaning the seal means by wiping access between the arms and across the seal means outer surface and adjacent portions of the housing exterior wall.

5. The sample site of claim 4, wherein the blunt cannula is a part of a male Luer lock connector, the sample site further comprising:
   flange means on the arms for securing the male Luer lock connector to the sample site with the tip thereof through the aperture.

6. The sample site of claim 1 further comprising:
   means for holding the blunt cannula to the sample site.

7. The sample site of claim 1, wherein the blunt cannula is the tip of a male Luer connector, the sample site further comprising:
   a pair of female Luer connector portions extending away from the housing about the aperture for receiving the male Luer connector tip, the female Luer connector portions being spaced apart to facilitate cleaning the seal means by wiping access between the connector portions and across the seal means outer surface and adjacent portions of the housing exterior wall.

8. The sample site of claim 7, the female Luer connector portions being affixed at respective locations to the housing exterior surface adjacent the aperture.

9. The sample site of claim 7, wherein the exterior wall includes an annular portion completely surrounding the aperture, the sample site further comprising:

hinge means connected to the housing remote from the aperture and supporting the female Luer connector portions, the hinge means having a first position for urging the connector portions away from the aperture to provide unobstructed access to the seal means outer surface and the annular portion of the exterior wall completely surrounding the aperture, and the hinge means having a second position in which the female Luer connector portions are placed in operative relationship with the aperture for receiving the male Luer connector tip therethrough.

10. A sample site adapted to connect to a blunt cannula comprising:

a housing;

a liquid path extending into the housing;

an actuator member fixedly positioned within the housing and having a lumen therethrough in fluid communication with the liquid path;

an apertured exterior wall on the housing through which the blunt cannula can enter the housing to make fluid connection to the lumen;

seal means adjacent the exterior wall aperture and presenting an outer surface generally flush with the housing exterior wall for normally sealing the aperture against fluid communication with the lumen, the seal means being movable into the actuator member under pressure of the blunt cannula passing into the aperture so as to open a channel in the seal means and expose the lumen therethrough to the blunt cannula, the seal means channel being resealed and the exterior wall and seal means outer surface being substantially unobstructed with the blunt cannula removed; and means for holding the blunt cannula to the sample site.

11. The sample site of claim 10, the housing including at least one port coupled to the liquid path.

12. The sample site of claim 10, the housing including first and second spaced apart ports at respective ends of the liquid path.

13. A sample site adapted to connect to a blunt cannula comprising:

a housing;

a liquid path extending into the housing;

an actuator member fixedly positioned within the housing and having a lumen therethrough in fluid communication with the liquid path;

an apertured exterior wall on the housing through which the blunt cannula can enter the housing to make fluid connection to the lumen;

seal means adjacent the exterior wall aperture and presenting an outer surface generally flush with the housing exterior wall for normally sealing the aperture against fluid communication with the lumen, the seal means being movable into the actuator member under pressure of the blunt cannula passing into the aperture so as to open a channel in the seal means and expose the lumen therethrough to the blunt cannula, the seal means channel being resealed and the exterior wall and seal means outer surface being substantially unobstructed with the blunt cannula removed; and a pair of arms extending away from the housing about the aperture for receiving the blunt cannula therethrough, the arms being spaced apart to facilitate cleaning the seal means by wiping access between the arms and across the seal means outer surface and adjacent portions of the housing exterior wall.

14. The sample site of claim 13, wherein the blunt cannula is part of a male Luer lock connector, the sample site further comprising:

flange means on the arms for securing the male Luer lock connector to the sample site with the tip thereof through the aperture.

15. The sample site of claim 13, the housing including at least one port coupled to the liquid path.

16. The sample site of claim 13, the housing including first and second spaced apart ports at respective ends of the liquid path.

17. A sample site adapted to connect to the tip of a male Luer connector comprising:

a housing;

a liquid path extending into the housing;

an actuator member fixedly positioned within the housing and having a lumen therethrough in fluid communication with the liquid path;

an apertured exterior wall on the housing through which the Luer connector tip can enter the housing to make fluid connection to the lumen;

seal means adjacent the exterior wall aperture and presenting an outer surface generally flush with the housing exterior wall for normally sealing the aperture against fluid communication with the lumen, the seal means being movable into the actuator member under pressure of the Luer connector tip passing into the aperture so as to open a channel in the seal means and expose the lumen therethrough to the Luer connector tip, the seal means channel being resealed and the exterior wall and seal means outer surface being substantially unobstructed with the Luer connector tip removed; and a pair of female Luer connector portions extending away from the housing about the aperture for receiving the male Luer connector tip, the female Luer connector portions being spaced apart to facilitate cleaning the seal means by wiping access between the connector portions and across the seal means outer surface and adjacent portions of the housing exterior wall.

18. The sample site of claim 17, the female Luer connector portions being affixed at respective locations to the housing exterior surface adjacent the aperture.

19. The sample site of claim 17, wherein the exterior wall includes an annular portion completely surrounding the aperture, the sample site further comprising:

hinge means connected to the housing remote from the aperture and supporting the female Luer connector portions, the hinge means having a first position for urging the connector portions away from the aperture to provide unobstructed access to the seal means outer surface and the annular portion of the exterior wall completely surrounding the aperture, and the hinge means having a second position in which the female Luer connector portions are placed in operative relationship with the aperture for receiving the male Luer connector tip therethrough.

20. The sample site of claim 17, the housing including at least one port coupled to the liquid path.

21. The sample site of claim 17, the housing including first and second spaced apart ports at respective ends of the liquid path.

22. A sample site adapted to connect to a blunt cannula comprising:
 a housing;
 a liquid path extending into the housing;
 an apertured exterior wall on the housing through which the blunt cannula can enter the housing to make fluid connection to the liquid path;
 seal means adjacent the exterior wall aperture and presenting an outer surface generally flush with the housing exterior wall for normally sealing the aperture against fluid communication with the liquid path, the seal means being openable under pressure of the blunt cannula passing into the aperture whereby to permit fluid connection thereof with the liquid path, the seal means resealing after removal of the blunt cannula; and
 a pair of arms extending away from the housing about the aperture for receiving the blunt cannula therethrough, the arms being spaced apart to facilitate cleaning the seal means by wiping access between the arms and across the seal means outer surface and adjacent portions of the housing exterior wall.

23. The sample site of claim 1 further comprising:
 means for holding the blunt cannula to the sample site.

24. The sample site of claim 22, wherein the blunt cannula is part of a male Luer lock connector, the sample site further comprising:
 flange means on the arms for securing the male Luer lock connector to the sample site with the tip thereof through the aperture.

25. A sample site adapted to connect to a male Luer connector comprising:
 a housing;
 a liquid path extending into the housing;
 an apertured exterior wall on the housing through which a tip of the male Luer connector can enter the housing to make fluid connection to the liquid path;
 seal means adjacent the exterior wall aperture and presenting an outer surface generally flush with the housing exterior wall for normally sealing the aperture against fluid communication with the liquid path, the seal means being openable under pressure of the male Luer connector when the tip passes into the aperture whereby to permit fluid connection thereof with the liquid path, the seal means resealing after removal of the male Luer connector tip; and
 a pair of female Luer connector portions extending away from the housing about the aperture for receiving the male Luer connector tip therethrough, the female Luer connector portions being spaced apart to facilitate cleaning the seal means by wiping access between the connector portions and across the seal means outer surface adjacent portions of the housing exterior wall.

26. The sample site of claim 25 the female Luer connector portions being fixedly connected at respective locations to the housing exterior surface adjacent the aperture.

27. The sample site of claim 25 wherein the exterior wall includes an annular portion completely surrounding the aperture, the sample site further comprising:
 arm means connected to the housing remote from the aperture and supporting the female Luer connector portions, the arm means having a first position for urging the connector portions away from the aperture to provide unobstructed access to the seal means outer surface and the annular portion of the exterior wall completely surrounding the aperture and, the arm means having a second position in which the female Luer connector portions are placed in operative relationship with the aperture for receiving the male Luer connector tip therethrough.

28. The sample site of claim 27, the arm means being hingedly connected to the housing and normally being in the first position and moveable to the second position by pressure applied against the arm means.

29. The sample site of claim 27, the arm means being slidably connected to the housing and slidable relative the aperture, the arm means being in the first position slid away from the aperture and in the second position slid toward the aperture.

30. The sample site of claim 25 wherein the housing includes a support portion attached thereto and the exterior wall includes an annular portion completely surrounding the aperture, the sample site further comprising:
 a frame member slidably received over the support portion;
 hinge arm means connected to the frame member and supporting the female Luer connector portions for sliding movement with the frame member, the frame member being slidable between a first position whereat the female Luer connector portions are in operative relationship with the aperture for receiving the male Luer connector tip therethrough, and a second position whereat the female Luer connector portions are in inoperative relationship with the aperture to provide unobstructed access to the seal means outer surface and the annular portion of the exterior wall completely surrounding the aperture.

31. The sample site of claim 30 the apertured exterior wall and support portion being disposed on opposite ends of the housing, the hinge arm means extending alongside an intermediate wall therebetween, the first position of the frame member being defined with the frame member adjacent the intermediate wall whereat the hinge arm means are spaced closely adjacent the intermediate wall, the second position of the frame member being defined with the frame member spaced away from the intermediate wall whereat the hinge arm means are urged outwardly from the intermediate wall and the female connector portions are spaced closely adjacent the intermediate wall.

32. The sample site of claim 25 the housing including at least one port coupled to the liquid path.

33. The sample site of claim 25, the housing including first and second spaced apart ports at respective ends of the liquid path.

34. The sample site of claim 33 the first and second ports being disposed on opposite sides of the housing with the apertured exterior wall being positioned therebetween so as to define a T-connection.

* * * * *